United States Patent [19]

Farkas-Himsley

[11] Patent Number: 4,861,754

[45] Date of Patent: Aug. 29, 1989

[54] BACTERIOCINS AND COMPOSITIONS THEREOF IN ANTI-VIRAL TREATMENT

[76] Inventor: Hannah Farkas-Himsley, 21 Edgar Avenue, Toronto, Ontario, M4W 2B1, Canada

[21] Appl. No.: 54,321

[22] Filed: May 26, 1987

Related U.S. Application Data

[63] Continuation-in-part of Ser. No. 868,250, May 28, 1986, abandoned.

[51] Int. Cl.$^4$ .................. A01N 25/00; A61K 37/02; C07G 7/02
[52] U.S. Cl. ............................. 514/2; 514/21; 514/885; 424/405; 424/92; 530/350; 530/825
[58] Field of Search .............................. 514/2, 21, 885; 424/405, 92; 530/350, 806, 825

[56] References Cited

PUBLICATIONS

Saito et al., Chemical Abstracts, vol. 91, No. 84180y (1979).
Saito et al., "Effects of a Bacteriocin from Mycobacterium Smegmatis on BALB/3T3 and Simian Virus 40 Transformed BALB c Mouse Cells" Microbiol. Immunol., vol. 25 (1), 13–22, Jan./1981.
Saito et al., "Effect of a Bacteriocin Produced by Mycobacterium Smegmatis on Growth of Cultured Tumor and Normal Cells" Cancer Research 39, 5114–5117, Dec./1979.
Watanabe et al., "Cytotoxicity of Pyocin 52 to Tumor and Normal Cells and its Interaction with Cell Surfaces" Biochim. et Biophysica Acta 633 (1980) 77–86.
Sypula et al., "Effect of Bacteriocins on Interferon Production" Arch. Immun. Ther. Exp., 25, 651–653, 1977.
Musclow et al., "Bacteriocin and Flow Cytometry in Laboratory Diagnosis of Leukemic Peripheral Blood Lymphocytes and Bone Marrow Cells" Eur. J. Cancer Clin. on Col., vol. 19, No. 2, pp. 163–171, 1983.
Farkas-Himsley, "Bacteriocins as Growth Inhibitors of Neoplastic and Tumorigenic Cells" IRCS Journal of Medical Science, vol. 4, pp. 291–295, Jul. 1976.

*Primary Examiner*—John Kight
*Assistant Examiner*—Nathan M. Nutter
*Attorney, Agent, or Firm*—Wyatt, Gerber, Burke & Badie

[57] ABSTRACT

It has been found that bacteriocins are able to kill virally-infected mammalian cells, including virally infected white blood cells. Accordingly, viral infections can be detected and ultimately treated using the bacteriocins and the methods described herein. The invention is particularly suited to detection and treatment of AIDS infection and infectious mononucleosis infection.

36 Claims, No Drawings

BACTERIOCINS AND COMPOSITIONS THEREOF IN ANTI-VIRAL TREATMENT

BACKGROUND OF THE INVENTION

This application is a continuation-in-part of U.S. application Ser. No. 06/868,250 filed May 28, 1986 and now abandoned.

White blood cells comprise, among other components, T and B cells (lymphocytes).

Of the viruses which are known to infect T-cells, the virus of extreme medical importance among these is HTLV-III, a retrovirus, which has recently been identified as the virus responsible for Acquired Immune Deficiency Syndrome or AIDS. It has been shown that the HTLV-III virus (currently known as HIV), involved in AIDS, can infect the $T_4$ cells in the blood and eventually destroy them. The $T_8$ suppressor cells are not subject to such infections.

Another medically important viral infection is infectious mononucleosis caused by the Epstein-Barr virus (EBV). A vast number of other mammalian cell-infecting viruses are known and include the Influenza viruses as well as others.

The AIDS virus is, of course, a particularly acute medical problem currently, with no proven curative effective antidote yet being generally available. The AIDS virus may infect the T-cells of a patient's blood and lie dormant therein for extended periods of time. However, when some factor triggers its replication, it rapidly effects the host T-cells, until they are incapable of performing their immune function against body invaders.

Researchers have previously identified and isolated bacterial-derived proteins now referred to as bacteriocins. These proteins are produced by a wide variety of bacteria, both Gram-positive and Gram-negative, and are named after the producer strain. Bacteriocins interact with specific bacterial strains normally closely related to the producer strain and prevent their multiplication by killing them. The specificity lies in the antigenic heterogeneity of the bacteriocins and their interaction with specific receptors on the surface of the sensitive strains of bacteria. Bacteriocins may vary in their mode of attack on their target bacteria. They may act by inhibiting all macromolecular synthesis, or by inhibiting selective electron transport-dependent processes, affecting $K+$ transport and ATP production. Some bacteriocins may interact with ribosomes thus specifically affecting protein synthesis; others will inhibit cell growth by causing degradation of DNA. Bacteriocins which share common modes of action are not necessarily structurally or antigenically related.

The utility of bacteriocins as selective inhibitors of the growth of neoplastic and tumorigenic cells has recently been recognized and reported. In the *ICRS Journal of Medical Science*, vol. 4, pp 291-295, July 1976, Farkas-Himsley reports the ability of the bacteriocin pyocin 1-4 to inhibit the growth of tumors induced by KHT fibrosarcoma cells in mice while remaining non-toxic to the non-tumorous cells. In Eur. *J. Clin, Oncol,* 19, 163-171 (1983) researchers report on the ability of colicin HSC-10, a bacteriocin, to inhibit the growth of leukemic peripheral blooc lymphocytes in a selective fashion over the normal lymphocytes and the non-cancerous neighbouring bone marrow cells.

The ability of bacteriocins to discriminate malignant cells from healthy cells has lead to speculation as to the specific mode of action of the bacteriocin on the target malignant cells. An hypothesis has been proposed which suggests that the oncogenic phenotype of the malignant cell is recognized by the bacteriocin and leads eventually to incorporation and interaction of the bacteriocin with its ultimate target, the metabolic or genetic machinery within the target cell. This hypothesis is supported by the observation that normal, healthy cells, lacking the oncogenic phenotype and the capacity for metastasis, are not harmed by the bacteriocin.

SUMMARY OF THE INVENTION

It is an object of the present invention to provide a means for detecting virally infected mammalian cells.

It is a further object of the present invention to provide substances and compositions which can be used in the therapy of various virally induced infections and diseases.

The present invention is based on the observation that bacteriocins are able to discriminate between virally infected mammalian cells and healthy, normal mammalian cells. This observation is to be contrasted with previous observations of bacteriocin attack on cancerous cells, given previous speculation that bacteriocins recognize elements of the cell morphology which are manifested by the oncogenic state of the malignant cell. Malignant cells are believed generally to possess cell membrane constituents which endow the cell with its non-self-limiting, non-regualted growth properties which in turn allow for metastasis. On the other hand, virally infected mammalian cells which are not malignant are self-limiting with regard to their growth patterns. Such cells are not known at present to be receptive to the mode of action of bacteriocin.

As used herein, the term "malignant" means "having the property of locally invasive and destructive growth and metastasis", i.e. as defined in Stedman's *Medical Dictionary*, 24th Edition, Williams & Wilkins, Baltimore, London, 1982.

Accordingly, it should be readily understood that the virally-infected mammalian cells referred to herein are not tumorigenic or malignant cells in that the virally infected mammalian cells have self-limiting growth and possess a growth pattern which is, prima facie, uncharacteristic of malignant cells.

According to the present invention, therefore, bacteriocins and compositions thereof are provided for use in treating virally infected mammalian cells.

There is also provided, within the scope of this invention, a means for detecting the growth of virally infected non-malignant mammalian cells which comprises treating these cells with bacteriocins and compositions thereof.

The bacteriocins useful in the present invention appear to have a recognition site within their chemical structure which will specifically and selectively interact with the virally infected cell. Moreover, appropriate dosages of the bacteriocins appear to kill selectively the virally infected cells whilst leaving the normal, healthy cells substantially unaffected.

Such bacteriocins are, in many instances, the same as those which discriminately kill or inhibit growth of various cancer cells such as fibrosarcoma, acute lymphoblastic leukemia (ALL), cervical carcinoma, adenocarcinoma, squamous cell carcinoma, chronic myelogenous leukemia, prolymphocytic leukemia, mastocytoma and many others. Specific examples of bacteriocins useful in the preesnt invention include pyocins, vibriocins, mycobacteriocins and colicins. Especially preferred for use herein are pyocin I-4 and colicin HSC10.

Virally-infected, non-malignant, mammalian cells may be detected within this invention by the treatment of these cells with bacteriocin. More specifically, cells infected by viruses can be detected by cell growth or cell death of the bacteriocin treated cells.

There are a number of methods known to those skilled in the art, including, but not limited to, binding assays (enzyme-linked, fluorescent and radiobinding), and metabolic uptake assays including the uptake of tritiated thymidine, flow-cytometry, that could effectively be used for detecting virallyinfected, non-malignant cells treated with bacteriocin.

The bacteriocins can be prepared using the known, standard techniques of bacterial fermentation using a strain of bacteria which has the potential for bacteriocin production. The bacteria are grown in a fermenter to the exponential phase. Induction follows, by use of a suitable chemical or physical agent, which will cause most of the cells (90-99 percent of them), to synthesize bacteriocin. An example of a suitable inducer is mitomycin C, at a level of about 0.5 micrograms per millilitre. Then the cells are further incubated. In the case of some cultures, the bacteriocin is secreted into the fermentation medium. In other cases, the cultures will not release the bacteriocin so that the cell wall needs to be broken up. This may be done under pressure (20000 psi for example) using a French pressure cell. The crude bacteriocin may be separated from the cell debris by centrifugation and is then contained in the supernatant liquid.

Having recovered the supernatant, standard biochemical separation processes can be used to purify the bacteriocin. For example, ammonium sulphate is preferably used at various concentrations, initially. Residual ammonium sulphate is then removed by dialysis against water. Then the precipitate containing the desired bacteriocin may be chromatographed on a column such as a Sephadex DEAE-50 a weak cation exchanger, and its various proteins separated by monitoring absorbance at 280 nm. Active fractions can be determined from among the proteins thus separated, and selected on the basis of the efficacy with which aliquots thereof kill bacterial strains known to be sensitive to the bacteriocin i.e., the indicator strain. Active protein fractions are then pooled. Further purification may be carried out by high performance liquid chromatography (HPLC) based on the charge of the proteins. The various peaks obtained by monitoring absorbance at 280 nm may be separated and again tested for activity against the indicator strain. Final purity of the protein bacteriocin may determined by sodium dodecyl sulphate polyacrylamide gel electophoresis (SDSPAGE). The presence of one major band after staining with Coomassie blue, indicates that purity of bacteriocin has been attained. An example of vibriocin and colicin purification appears in *Microbios*, 1969, 1B 87-89 and *Cytobios*, 1985, 42: 193-207, respectively.

Thus, the selection isolation and purification of appropriate bacteriocins for use in the present invention is well within the skill of the art. Routine bacteriocin production and screening procedures as described above will readily yield to the skilled worker specific bacteriocins which are active against virally infected mammalian cells. Whilst the following description of specific preferred embodiments of the invention describes individual specific bacteriocins which have been found to be active and effective against specific virally infected B and T-cells as described, the invention is by no means limited to the use of the specific exemplified bacteriocins.

The bacteriocins useful in the present invention should be used in relatively small amounts, to safeguard against toxicity problems. In toxicity studies conducted on mice, the effective repeated dose of ten micrograms per animal was 100% effective without any toxic effects on the mice. However, with increasing concentrations of bacteriocins, toxicity was apparent. With mice of strain C3H/J, 80 to 100 micrograms per mouse were fatal. With other species of mice, such as hybrid C3DX2F1/J a ten-fold greater resistance than for C3H/J mice was noted, and toxicity was reached at 1000 micrograms per mouse.

On the basis that a unit does of the bcteriocin is preferably aimed at affecting one million virally infected cells, it is preferred to administer from 0.01 ug-10 ug bacteriocin per treatment, preferably from 0.1 ug to 1 ug per treatment. Repeated doses of this size may be administered. It is preferred that bacteriocin be added to a given lymphocyte population to arrive at a ratio of $10^{-5}$ ng to $10^{-2}$ ng bacteriocin per target cell, most preferably, $10^{-4}$ ng to $10^{-3}$ ng per target cell. This dosage size is significantly smaller than the dose required to treat cancerous cells.

Where the compositions of the invention are to be used will dictate the dosage form of the composition. Because the bacteriocins are proteins and will be digested by stomach enzymes, and also because, preferably, the compositions are used in attack on lymphocytes, the compositions are preferably prepared as solutions for administration by injection. Accordingly, preferred carriers are buffered and saline aqueous media. Such solutions are formulated according to standard practice in the art.

The invention is further illustrated in the following specific examples:

EXAMPLE 1

Preparation of Bacteriocin HSC10

To two hundred litres of Brain Heart Infusion medium (BHI) (Difco Labs, Detroit, Mich.) was added an inoculum of the bacterial producer strain *E. coli* HSC-10 which had been grown overnight. The culture was grown at 37° until the bacterial growth reached the exponential phase. An inducer, namely Mitomycin C in the amount of 0.5 micrograms per ml was then added to the culture and growth was allowed to continue for a further 4-5 hours.

The resulting broth was spun on a Sharples centrifuge, for ninety minutes, to form a supernatant broth which was discarded, and a pellet of solid and semi-solid material. The pellet had a wet mass of 505 g. The cellular material within the pellet was then disrupted using a French pressure cell and the resultant material was resuspended in 1% of its original volume of Tris (0.05M, ph 7.8). The resulting suspension was spun, and the pellet of debris discarded. The supernatant material so obtained, containing the lysate which contained the crude bacteriocin, was worked up and purified as described below in Example 2.

EXAMPLE 2

Purification of Bacteriocin

The supernatant containing the crude bacteriocin obtained in Example 1 was freed from proteins other than the active bacteriocin by ammonium sulphate precipitation at various concentrations. The protein which salted out at a concentration of 35-50% of ammonium sulphate in the supernatant liquid was retained, and the supernatant discarded. The retained material was dialysed against water, spun at 46,000xg, and the resultant supernatant stored at $-20°$ C. prior to subsequent purification.

After thawing, the frozen supernatant was subjected to chromatography using Sephadex - DEAE A-50 and collected in separate fractions using 0.0-1.0M NaCl in 0.01M Tris, pH 8.2 as eluant and monitoring absorbance at 280 nm.

Fractions of interest were then pooled and tested for activity against the indicator strain E. coli Y10 using the turbidity test. Specifically, the indicator strain grown overnight in brain heart infusion medium at 37° C. was used as inoculum to obtain exponential growth to a specific cell number. These bacteria were mixed with two-fold dilutions of the partially purified bacteriocin as described above and growth inhibition of the indicator strain was recorded spectrophotometrically. Growth response curves were generated by these turbidity measurements from which the lethal units/ml of the colicin HSC10 was calculated in view of the known concentration of bacteriocin added to the known number of cells of the indicator strain n the medium. The LU50, lethal units per ml required to kill 50% of the indicator strain population, is shown in and discussed with reference to Table 1 hereinafter.

Further purification of the pooled fractions was carried out using high performance liquid chromatography (HPLC) and those fractions collected at peak absorbance of 280 nm were pooled and aliquots thereof subjected to the same turbidity test as described above.

The purity of this final fraction was determined by SDS-PAGE analysis by which, after staining with Coomassie blue, the purity of the bacteriocin was confirmed by the presence of one major band.

The amounts of bacteriocin recovered at each step in the method described above and the bavcteriocidal activity of those amounts is recorded in Table 1 appearing below:

generate necessary amounts of bacteriocin. The method of purification preferred herein was sufficient to establish a purification factor, based on the bacteriocidal activity of the protein, of 930 at which only 0.63 ug of bacteriocin is required to inhibit growth of 50% of the indicator strain population. The fraction that is isolated for further study in Examples 3, 4 and 5, and referred to hereinbelow as HSC-10 is derived from the precipitate after the Sephadex DEAE - A50 treatment.

EXAMPLE 3

Selectivity of Colicin HSC10 in Identifying Virally Infected Leukocytes in vitro Lymphocytes obtained from 14 different AIDS patients were enriched on Ficoll-Paque TM (Pharmacia Fine Chemicals, Dorval, Quebec), counted and divided into experimental and control groups. Colicin HSC10, extracted and purified as described above, was diluted in tris buffer at pH 7.4 and added to the experimental lymphocyte population to arrive at a raio of $10^{-5}$ to $10^{-2}$ ng bacteriocin per target cell. The control population received only the tris-buffer diluent.

The two cell populations were distributed into microwells and grown overnight in the preesnce of $^3H$=thymidine at 37° C. in the presence of 5% $CO_2$ humidified air. Thereafter, the cells were harvested, washed free of excess $^3H$-thymidine and passed through a scintillation counter to evaluate uptake of radioactivity which is a reflection of cell metabolism and growth. The effect of bacteriocin was evaluated by % reduction of disintegrations per minute (dpm) in the bacteriocin treated group as compared to the control groups.

In a parallel experiment, bacteriocin was added to lymphocytes obtained from 9 healthy individuals and compared, via the $^3H$-thymidine uptake test, with control healthy lymphocytes subjected only to the tris-buffer bacteriocin diluent.

A third group comprising three patients in high-risk AIDS group (e.g. haemophiliacs) were tested, although the presence of AIDS in these patients was not confirmed.

$^3H$-thymidine uptake in each of the three groups was measured as a percent of the control group, which was, in each case, patients in the respective groups without bacteriocin treatment.

In the concentrations applied, the bacteriocin exhibited effects on the number of HTLV-III infected (AIDS) lymphocytes from the AIDS patients, and on

TABLE I

| | Purification Data for Colicin $HSC_{10}$ | | | | |
|---|---|---|---|---|---|
| | PROTEIN | | BACTERIOCIN POTENCY[a] | | |
| Test Material | Total (mg) | % of original | $LU_{50}$ (ug/ml) | Specific activity | Purification factor |
| Crude Lysate | 15,674 | 100 | 0.67 | $4.3 \times 10^{-5}$ | |
| PPT. 35-50 (percent cut) | 1,298 | 8.28 | 0.56 | $4.3 \times 10^{-4}$ | 10 |
| PPT. 35-50% after Sephadex DEAE - A50 | 139.8 | .89 | 0.16 | $1.1 \times 10^{-3}$ | 26 |
| Active Material from Sephadex after HPLC - DEAE | 15.9 | .10 | 0.63 | $4.0 \times 10^{-2}$ | 930 |

[a]Tested against bacteria by turbidity test.

It will be noted that the amount of colicin HSC10 derived from the culture lysate is only about 0.10% of the original weight of the lysate, suggesting that, preferably, large volumes of bacteria are cultured in order to the lymphocytes from the AIDS suspects and the healthy, normal individuals as shown by Table II below:

TABLE II

| | $^3$H—thymidine uptake as a % of control | | Number of test results in each category |
|---|---|---|---|
| | range | average | |
| AIDS Patients | | | |
| 15 tests (on 14 different patients) | | | |
| Inhibition | 20–86 | 53 | 8 out of 15 (53%) |
| | | | (7 out of 14 patients) |
| Borderline | | | |
| Inhibition | 99–105 | 102 | 2 out of 15 (13%) |
| | | | (2 out of 14 patients) |
| Stimulation | >110 | 270 | 5 out of 15 (33%) |
| | | | (5 out of 14 patients) |
| AIDS Suspected | | | |
| 3 tests (on 3 different patients) | | | |
| Inhibition | — | | 0 out of 3 |
| Borderline | | | |
| Inhibition | 100–111 | 105 | 2 out of 3 |
| (90–110) | | | |
| Stimulation | >110 | 145 | 1 out of 3 |
| Normals | | | |
| 14 tests (on 9 different individuals) | | | |
| Inhibition | 43–67 | 51 | *4 out of 14 (29%) |
| | | | (4 out of 9 individuals) |
| Borderline | | | |
| Inhibition | 90–95 | 93 | 2 out of 14 (14%) |
| (90–110) | | | (2 out of 9 individuals) |
| Stimulation | >110 | 166 | 8 out of 14 (57%) |
| | | | (6 out of 9 individuals) |

*As described hereinabove, four tests from samples from individuals in the "Normal" group, known not to have the AIDS virus, were sensitive to bacteriocins in the $^3$H thymidine inhibition test, which is indicative of a viral infection. Three of these "four false-positive" individuals were later confirmed as having had other viral infections by the 2–5 A synthetase test. This latter test, described in *Journal of Infectious Diseases*, Read, S. E., et al September/85, is widely known and accepted in the art for the early diagnosis of viral infections. One of the "false-positive" individuals was believed to have had another viral infection by the $^3$H-thymidine test. In a later study, in accordance with a transient viral infection this fourth individual who reacted as "false-positive" exhibited stimulation, as opposed to inhibition of $^3$H-thymidine uptake. Accordingly, this false-positive individual is recorded in the Normal section of Table II under both inhibition and stimulation reflecting his variant test results. It is noteworthy that this individual showed inhibition in only one $^3$H-thymidine uptake test but in three later tests showed stimulation.

Yet another individual who is designated above as a "false-positive" is recorded in the Normal section of Table II under both inhibition and stimulation. This individual exhibited inhibition and, as described above, tested positive for a transient viral infection. This individual exhibited stimulation in the $^3$H-thymidine test presumably after his transient viral infection cleared up.

One of the Normal individuals exhibited borderline inhibition in one test and later exhibited stimulation in another test. This individual is recorded in Table II under both categories.

Of the fifteen tests performed on the AIDS patients, 53% showed an inhibition of thymidine uptake, with 13% showing borderline inhibition. Conversely, of the fourteen tests performed on the normal individuals, 57% showed an effective stimulation of thymidine uptake, with 14% showing borderline inhibition, and only 29% (4 out of 14) showing inhibition.

None of the three suspected AIDS patients showed sensitivity to bacteriocin. At the time of this testing, tests and observations confirmed that none of these patients carried the AIDS virus.

In summary, a remarkable effect can be observed from the results presented in Table II. Firstly, the number of AIDS lymphocytes exhibiting uptake of the radioactivity is significantly reduced when bacteriocin is introduced. Secondly, and importantly, growth of normal lymphocytes subjected to the same concentrations of bacteriocin appears not to be impaired (71%). Still more interestingly, 57% of those normal lymphocytes which were subjected to bacteriocin exhibited an increase in radioactivity count by comparison with those untreated. This signifies stimulation of growth of normal lymphocytes, a response which will presumably allow a substantial number of patients treated with bacteriocin greater immunity against other infections which attend AIDS patients.

To identify the target of bacteriocin attack on AIDS infected lymphocytes more specifically, monoclonal antibodies were employed. It is known that the ratio of sub-set helper-inducer ($T_4$) cells to sub-set suppressor ($T_8$) cells which interfere with the immune response of the AIDS patient, i.e. the $T_4/T_8$ ratio, is reduced in AIDS patients - see Evatt et al., *New England Journal of Medicine*, Vol. 313, page 483. The subset helper-inducer cells ($T_4$) which activate the immune responses and are therefore vital components of the body defenses, are infected with HTLV-III viruses and their function is impaired or non-existant. Experiments were therefore carried out in which specific monoclonal antibodies to $T_4$ cells (New England Nuclear, Catalogue No. NEN-038) and to $T_8$ cells (New England Nuclear, Catalogue No. NEI-039) were used to evaluate the presence and numbers of $T_4$ and $T_8$ lymphocytes after bacteriocin treatment of lymphocytes derived from an AIDS patient.

It was found that the numbers of subset $T_8$ suppressor lymphocytes remained unchanged after bacteriocin treatment whereas the number of the infected $T_4$ cells were significantly reduced.

Specifically, the test was performed using specific monoclonal antibodies to $T_4$ and $T_8$ cells, described above, prepared by a process entitled the Hybridoma Technique. This technique is widely applied by those skilled in the art.

The monoclonal antibodies to $T_4$ or $T_8$, thus prepared, are labelled with a fluorescent compound (e.g. fluorescein isothiocyanate) which may be detected due tot he fluorescence of the dye under ultra violet light.

The $T_4$ and $T_8$ cells are then associated with their respective fluorescent antibodies and counted under ultra violet light.

Each of the AIDS patients tested showed in the presence of bacteriocin a decrease of between 14–21% in their $T_4$ lymphocytes. Their $T_8$ lymphocytes were either not affected at all or nominally stimulated or inhibited.

Thus, according to the specific embodiment described herein, it has been shown that bacteriocins are effective in reducing the number of virally infected T-lymphocytes. More specifically, the utility of bacteriocins e.g. Colicin HSC-10, is established in reducing the number of $T_4$ cells without corresponding harm but rather stimulation to normal T cells.

EXAMPLE 4

The effect of bacteriocin on AIDS patients lymphocytes as well as lymphocytes infected with other viruses such as sore throat influenza and infectious mononucleosis can be determined by flow-cytometry using techniques similar to those disclosed in IRCS Medical Science, 11, 236–237 (1983).

In general, the method involves analysis of the DNA content of each cell in a given sample in order to assess the percentage of cells existing, at an instant, in a specific phase of the cell cycle. Since bacteriocins can affect sensitive cells by degradation of DNA resulting in nucleotide leakage, an increasing number of treated cells with little DNA can be detected by flow-cytometry. Cells sensitive to bacteriocin and treated therewith will commonly be seen to accumulate within the "pre-$G_1$" channels when the results are plotted on a histogram which signifies decreasing DNA content, since the DNA of these cells is degraded.

More specifically, lymphocytes obtained from patients previously diagnosed as having infectious mononucleosis (by infection with the Epstein-Barr virus) were isolated by Ficoll-Paque (Pharmacia Fine Chemicals, Montreal) and stained with propidium iodine. Colicin HSC-10, extracted and purified as in Example 1, was added to a sample of the isolated lymphocytes. Cell fluorescence was then measured during the growth cycle in a flow cytometer (FCM). Lymphocytes to be tested, to which no bacteriocin had been added, were used to calibrate the $G_0/G_1$ phase cells to that of the standard. The total cell number tested was obtained from numerical data print out. The percent of the total was calculated for the cells present in the "pre-$G_1$" and $G_0/G_1$ phases by integration of the cells under the peak. The final results were expressed following subtraction or addition of the percent change which occurred in the cell numbers of the controls i.e. the virally infected cells not exposed to bacteriocins.

The results are presented in Table III.

TABLE III

| Patient # | Test # | cells in "Pre-$G_1$" | Peak $G_0/G_1$ | $SG_2M$ | Sensitive |
|---|---|---|---|---|---|
| 1 | 1 | +33 | −14 | −31 | −2.0 | + |
|   | 2 | +24 | +17 | −24 | +0.2 | + |
| 2 | 3 | +17 | +11 | −18 | +1.0 | + |
|   | 4 | +21 | +30 | −22 | +1.3 | + |
| 3 | 5 | +15 | +14 | −13 | −2.6 | + |
| 4 | 6 | −2.4 | +13 | −5.1 | +7.6 | + |
| 5 | 7 | +0.5 | +4.6 | −0.8 | +0.3 | − |
| 6 | 8 | −4.3 | +7.5 | +2.0 | +2.2 | ± |
| 7 | 9 | +1.3 | −1.1 | −0.3 | −1.2 | − |

There were nine tests performed on seven individuals. Six of the seven patients tested showed on their histograms a decrease in cells from the $G_0/G_1$ phase (refer to column 5) and five out of seven patients exhibited an accumulation of cells in the "pre-$G_1$" phase (refer to column 3). In summary, in 78% of the tests, patients samples exhibited sensitivity to colicin HSC-10.

EXAMPLE 5

Four patients categorized as Normal in the first section of Example 3 and who appeared to have the flu by clinical symptoms, were found to have a transiently positive reaction with bacteriocins. These patients were subsequently tested positive for the presence of 2-5A synthetase, the presence of which is indicative of a viral infection (*J. Infectious Diseases*, Read, S. E., et al, September/85). After a period of time sufficient for recovery from the flu symptoms, these patients were retested for bacteriocin sensitivity and found to be negative. A tentative conclusion that can be drawn from these results is that at least some viral infections are favourably affected by bacteriocin HSC-10.

What is claimed is:

1. A method of inhibiting the growth of virally infected, non-malignant mammalian cells which comprises treating said cells with a growth inhibiting and viricidal amount of a bacteriocin.

2. The method according to claim 1 wherein said virally infected mammalian cells are white blood cells infected with a virus selected from the HTLV-III virus and the infectious mononucleosis virus.

3. The method according to claim 1 wherein said virally infected cells are T-cells infected with the HTLV-III virus.

4. The method according to claim 1 wherein the said virally infected cells are $T_4$ cells infected with the HTLV-III virus.

5. The method according to claim 2 wherein the bacteriocin is selected from pyocins, vibriocins, mycobacteriocins and colicins.

6. The method according to claim 3 wherein the bacteriocin is selected from pyocins and colicins.

7. The method according to claim 4 wherein the bacteriocin is selected from pyocins and colicins.

8. The method according to claim 4 wherein the bacteriocin is selected from pyocin I-4 and colicin HSC-10.

9. The method according to claim 4 wherein the bacteriocin is colicin HSC-10.

10. The method according to claim 1 wherein the cells are present in a biological sample obtained from a mammalian body, and are treated with an amount of bacteriocin in the approximate range from $10^{-5}$ ng to $10^{-2}$ ng per target cell.

11. The method according to claim 10 wherein the bacteriocin is HSC-10 and is administered in an amount in the approximate range from $10^{-4}$ ng to $10^{-3}$ ng per target cell.

12. The method according to claim 1 wherein the infected, non-malignant mammalian cells to be treated comprise lymphocytes contained in a living mammal.

13. The method according to claim 11 wherein the living mammal is administered a dose of bacteriocin in the approximate range of 0.01 ug to 10 ug.

14. The method of claim 13 wherein the bacteriocin is colicin HSC-10 and is administered in an amount in the approximate range 0.1 ug to 1 ug.

15. A pharmaceutical composition useful in inhibiting growth of and killing virally-infected mammalian cells which comprises from about 0.01 ug to 1.0 ug of bacteriocin per dose per 20 g bodty weight of the mammal as active ingredient in admixture with a pharmaceutically acceptable diluent.

16. The composition according to claim 15 wherein the bacteriocin is selected from pyocins, vibriocins, mycobacteriocins and colicins.

17. The composition according to claim 15 wherein the bacteriocin is selected from pyocin I-4 and colicin HSC-10.

18. The composition according to claim 15 wherein the bacteriocin is present in the composition in a range of about 0.1 ug to 1.0 ug. per dose per 20 g body weight of the mammal.

19. A method of treating a patient having a white blood cell viral infection selected from AIDS infections and infectious mononucleosis viral infection which comprises administering thereto an effective amount of a bacteriocin selected from pyocins, vibriocins, mycobacteriocins and colicins.

20. The method according to claim 19 wherein the patient has AIDS infection and the bacteriocin is colicin HSC-10.

21. The method according to claim 20 wherein the amount of colicin HSC-10 administered is sufficient to ensure treatment of the virally affected lymphocytes with an amount of bacteriocin in the approximate range of $10^{-5}$ ng to $10^{-2}$ ng per target cell.

22. The method according to claim 21 wherein the amount of bacteriocin administered is in the approximate range of $10^{-4}$ ng to $10^{-3}$ ng per target cell.

23. A method of detecting virally-infected, non-malignant mammalian cells by the interactions of said cells with bacteriocin.

24. A method of detected virally-infected, non-malignant mammalian cells by assessing cell growth inhibition after treatment with bacteriocin.

25. A method of detecting virally-infected, non-malignant mammalian cells by showing cell death after treatment with bacteriocins.

26. The method according to claims 23, 24 or 25 wherein said bacteriocin is selected from pyocins, vibriocins, mycobacteriocins and colicins.

27. The method according to claim 23, 24 or 25 wherein virally-infected non-malignant mammalian cells comprise lymphocytes.

28. The method according to claim 24 wherein cell growth is assessed by binding assays.

29. The method according to claim 24 wherein cell growth is assessed by measuring the uptake of a radioactive element by said cells.

30. The method according to claim 25 wherein cell death is shown by flow-cytometry.

31. A liquid preparation for use in in vitro diagnosis of virally infected non-malignant mammalian cells, said preparation comprising an amount of bacteriocin sufficient to obtain a ratio of between about $10^{-5}$ ng to $10^{-2}$ ng bacteriocin per virally infected non-malignant mammalian cell; and a pharmaceutically acceptable liquid carrier.

32. The preparation of claim 31 wherein the ratio is between about $10^{-4}$ ng to $10^{-3}$ ng.

33. The preparation of claim 31 comprising an aqueous suspension or solution of said bacteriocin.

34. The preparation of claim 33 wherein said suspension or solution is buffer.

35. The preparation of claim 34 wherein said buffer is selected from tris buffer or phosphate buffered saline.

36. The preparation of claim 32 wherein bacteriocin is colicin HSC-10.

* * * * *